(12) United States Patent
Ueda et al.

(10) Patent No.: US 10,159,827 B2
(45) Date of Patent: Dec. 25, 2018

(54) DISINFECTION CAP

(71) Applicant: TERUMO KABUSHIKI KAISHA, Shibuya-ku, Tokyo (JP)

(72) Inventors: Yasuhiro Ueda, Kofu (JP); Hitoshi Takeuchi, Kawasaki (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 377 days.

(21) Appl. No.: 14/865,612

(22) Filed: Sep. 25, 2015

(65) Prior Publication Data

US 2016/0088995 A1 Mar. 31, 2016

(30) Foreign Application Priority Data

Sep. 25, 2014 (JP) .................. 2014-195491

(51) Int. Cl.
*A61M 39/16* (2006.01)
*A61L 2/18* (2006.01)
*A61M 39/20* (2006.01)

(52) U.S. Cl.
CPC ............ *A61M 39/162* (2013.01); *A61L 2/18* (2013.01); *A61M 39/16* (2013.01); *A61M 39/20* (2013.01)

(58) Field of Classification Search
CPC ................ A61M 39/162; A61M 39/20; A61M 2205/0205

See application file for complete search history.

(56) References Cited

U.S. PATENT DOCUMENTS

| 5,190,534 A * | 3/1993 | Kendell ............... A61M 39/162 |
| | | 604/29 |
| 8,162,899 B2 * | 4/2012 | Tennican ............ A61M 39/165 |
| | | 604/191 |
| 8,628,501 B2 | 1/2014 | Hadden |
| 8,721,627 B2 * | 5/2014 | Alpert .................... A61M 39/16 |
| | | 604/265 |
| 2009/0137969 A1 * | 5/2009 | Colantonio ............... A61L 2/18 |
| | | 604/265 |

\* cited by examiner

*Primary Examiner* — Nathan R Price
*Assistant Examiner* — John Doubrava
(74) *Attorney, Agent, or Firm* — Buchanan Ingersoll & Rooney PC (57) ABSTRACT

A disinfection cap is provided with a cap main body and a wiping body held by the cap main body. The cap main body includes a cap side locking section that prevents pullout of the cap main body by engagement with a medical connector side locking section. The wiping body includes an impregnation section impregnated with an antiseptic solution and is movable with respect to the cap main body so as to wipe at least the surface of a top face wall, the inner peripheral face of an opening of the top face wall, or the surface of a valve body in a male connector connection section of a medical connector with the impregnation section with the cap side locking section engaged with the medical connector side locking section.

16 Claims, 9 Drawing Sheets

DISINFECTION CAP

CROSS-REFERENCES TO RELATED APPLICATIONS

This application claims priority to Japanese Patent Application No. 2014195491, filed on Sep. 25, 2014, the entire content of which is incorporated herein by reference.

TECHNICAL FIELD

The disclosure herein relates to a disinfection cap for a medical connector provided with a male connector connection section, in which a valve body which blocks an opening of a top face wall is pushed in to form a flow path when a male connector is connected thereto. The disinfection cap is and also provided with a medical connector side locking section which prevents pullout of the male connector by engagement with a male connector side locking section. The disinfection cap thus enables stable and sufficient wiping.

BACKGROUND DISCUSSION

Conventionally, when a medical connector as described above is used, the part of the male connector connection section which is required to be disinfected, such as the surface of the top face wall, the inner peripheral face of the opening of the tap face wall, and the surface of the valve body, is wiped with an alcohol swab prior to use. However, when the wiping is performed in such a manner, disinfection may be insufficient due to a difference in skill.

There are known disinfection caps used in such wiping. For example, U.S. Pat. No. 8,628,501 B2 describes a disinfection cap which is provided with an impregnation section impregnated with an antiseptic solution on the rear face of a cap main body. However, in such a disinfection cap, it is necessary to press the cap main body against a male connector connection section of a medical connector and then rotate the cap main body to perform wiping, while still maintaining such a pressed state. Thus, also in this case, disinfection may be insufficient due to a difference in skill.

Further, U.S. Pat. No. 8,721,627 B2 describes a disinfection cap which is provided with an impregnation section impregnated with an antiseptic solution on the rear face of a cap main body and a cap side inner thread section screwed with a medical connector side external thread section on a peripheral wall inner peripheral face of the cap main body. In such a disinfection cap, since the impregnation section impregnated with an antiseptic solution is pressed against a male connector connection section of a medical connector by attaching the cap main body to the medical connector, stable disinfection can be performed to some extent. However, it is difficult to sufficiently wipe off various germs and dirt.

SUMMARY

The disclosure herein has been made in view of the above circumstances, in order to provide a disinfection cap that enables stable and sufficient wiping.

A disinfection cap according to an exemplary embodiment of the disclosure is a disinfection cap for a medical connector, the medical connector including a male connector connection section, in which a valve body blocking an opening of a top face wall is pushed in to form a flow path when a male connector is connected thereto, and a medical connector side locking section configured to prevent pullout of the male connector by engagement with a male connector side locking section. The disinfection cap includes a cap main body which includes a cap side locking section configured to prevent pullout of the cap main body by engagement with the medical connector side locking section and a wiping body which is held by the cap main body and includes an impregnation section impregnated with an antiseptic solution. The wiping body is movable with respect to the cap main body so as to wipe at least a surface of the top face wall, an inner peripheral face of the opening, and/or a surface of the valve body in the male connector connection section with the impregnation section with the cap side locking section engaged with the medical connector side locking section.

Preferably, in the disinfection cap of the exemplary embodiment, the wiping body is rotatable around an axis of the male connector connection section with respect to the cap main body with the cap side locking section engaged with the medical connector side locking section.

Further, in the disinfection cap of the exemplary embodiment, the wiping body is movable along an axis of the male connector connection section with respect to the cap main body with the cap side locking section engaged with the medical connector side locking section.

Still further, in the disinfection cap of the exemplary embodiment, the wiping body is movable with respect to the cap main body so as to wipe at least the inner peripheral face of the opening with the impregnation section with the cap side locking section engaged with the medical connector side locking section.

Preferably, in the disinfection cap of the exemplary embodiment, the wiping body includes an operation section coupled to the impregnation section through a coupling section passing through a through hole formed on the cap main body.

The disclosure herein makes it possible to engage the cap side locking section of the cap main body with the medical connector side locking section to prevent pullout of the cap main body and, in this state, move the wiping body with respect to the cap main body to wipe at least the surface of the top face wall, the inner peripheral face of the opening of the top face wall, or the surface of the valve body with the impregnation section.

Thus, the disinfection cap according to the disclosure makes it possible to provide a disinfection cap that enables stable and sufficient wiping.

DETAILED DESCRIPTION

Hereinbelow, a disinfection cap according to an exemplary embodiment of the disclosure will be described in detail as an example with reference to FIGS. 1 to 5.

In the present specification, upper and lower directions indicate directions along the axis of a male connector connection section of a medical connector with the disinfection cap attached to the medical connector. Specifically, the upper side indicates a side on which an operation section of the medical connector is arranged (that is, the upper direction in FIGS. 1 and 6) and the lower side indicates an opposite side thereof.

Figure 1:
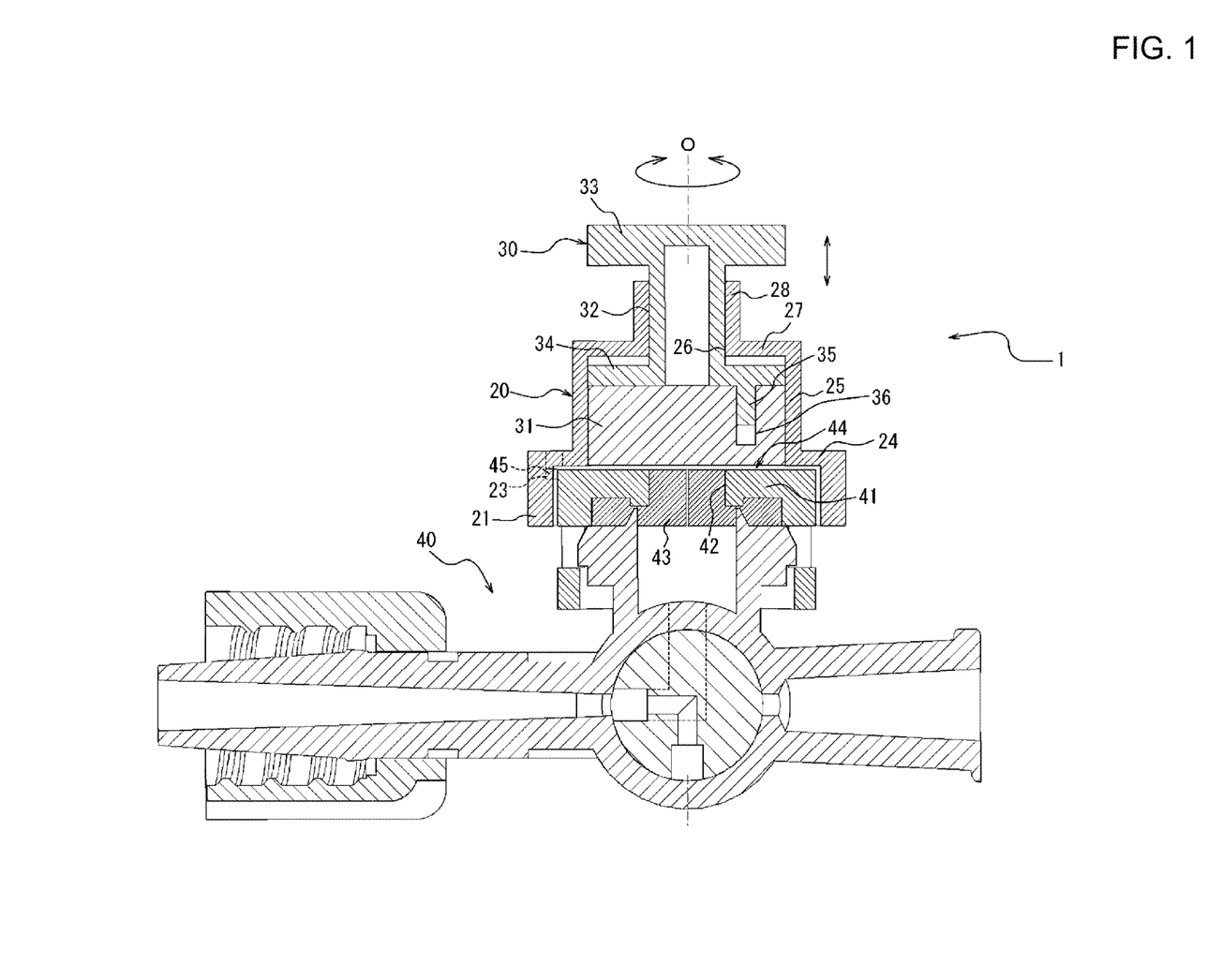
FIG. 1 is a longitudinal sectional view illustrating a state in which a disinfection cap according to an exemplary embodiment of the disclosure is attached to an example of a medical connector.
Figure 2:
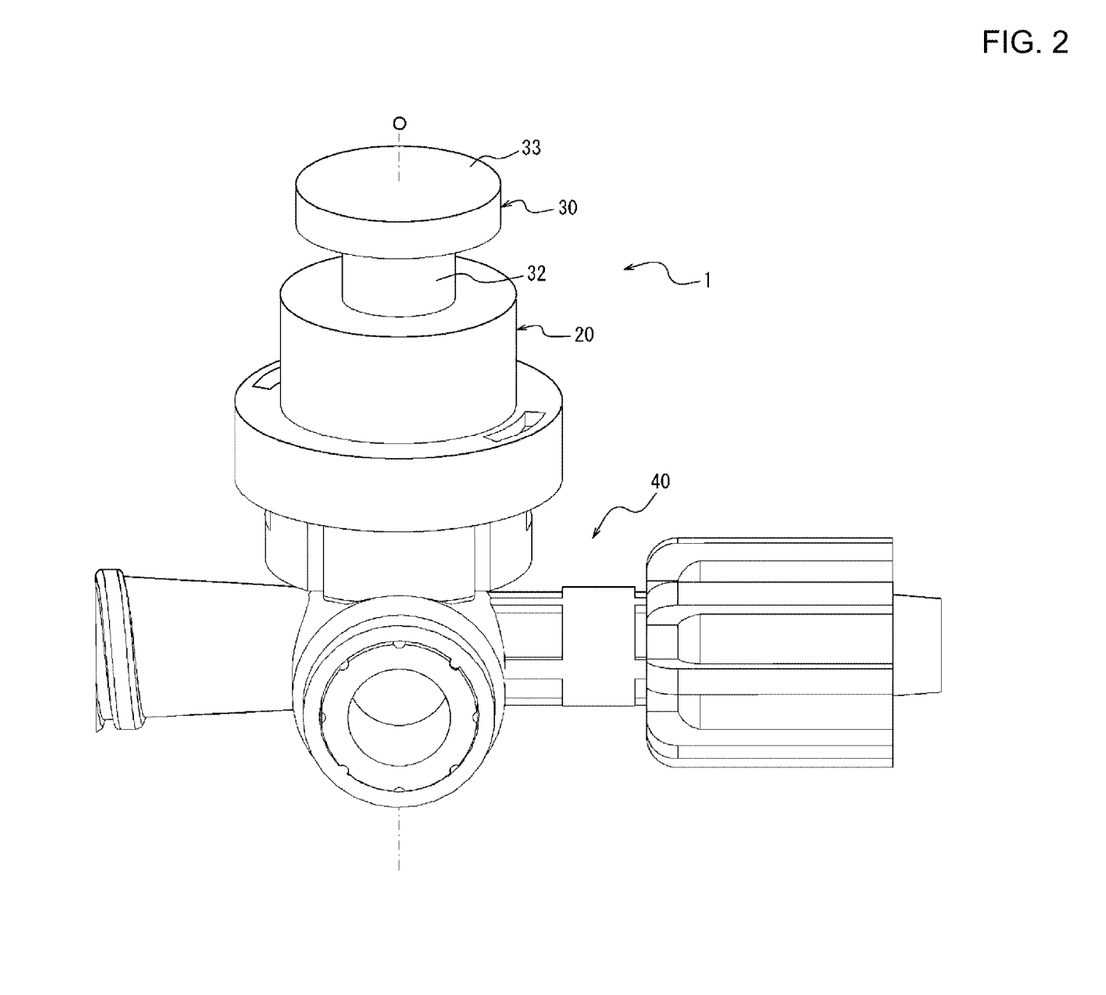
FIG. 2 is a perspective view of the disinfection cap and the medical connector of FIG. 1.
Figure 3:
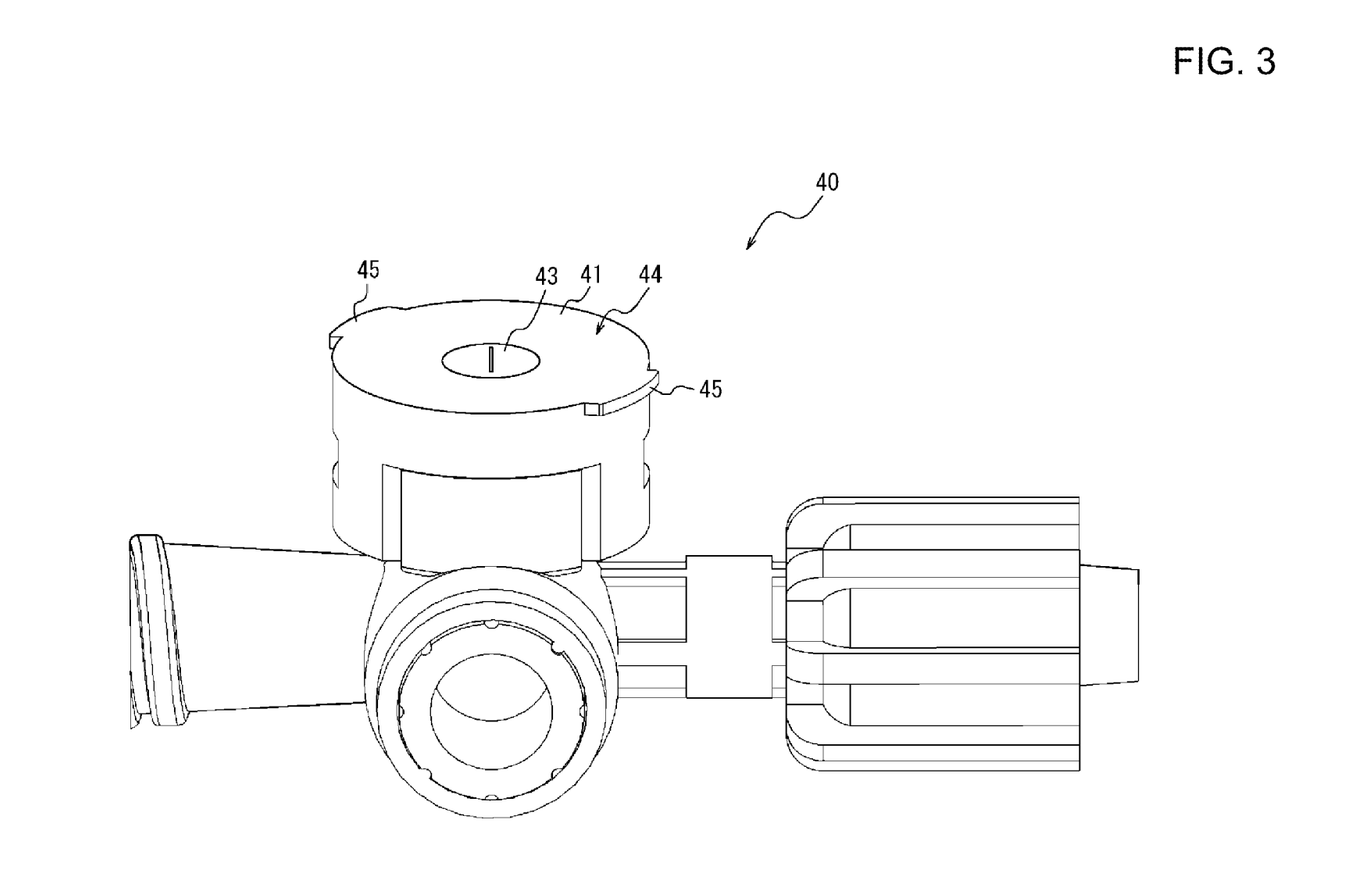
FIG. 3 is a perspective view of the medical connector of FIG. 1.
Figure 6:
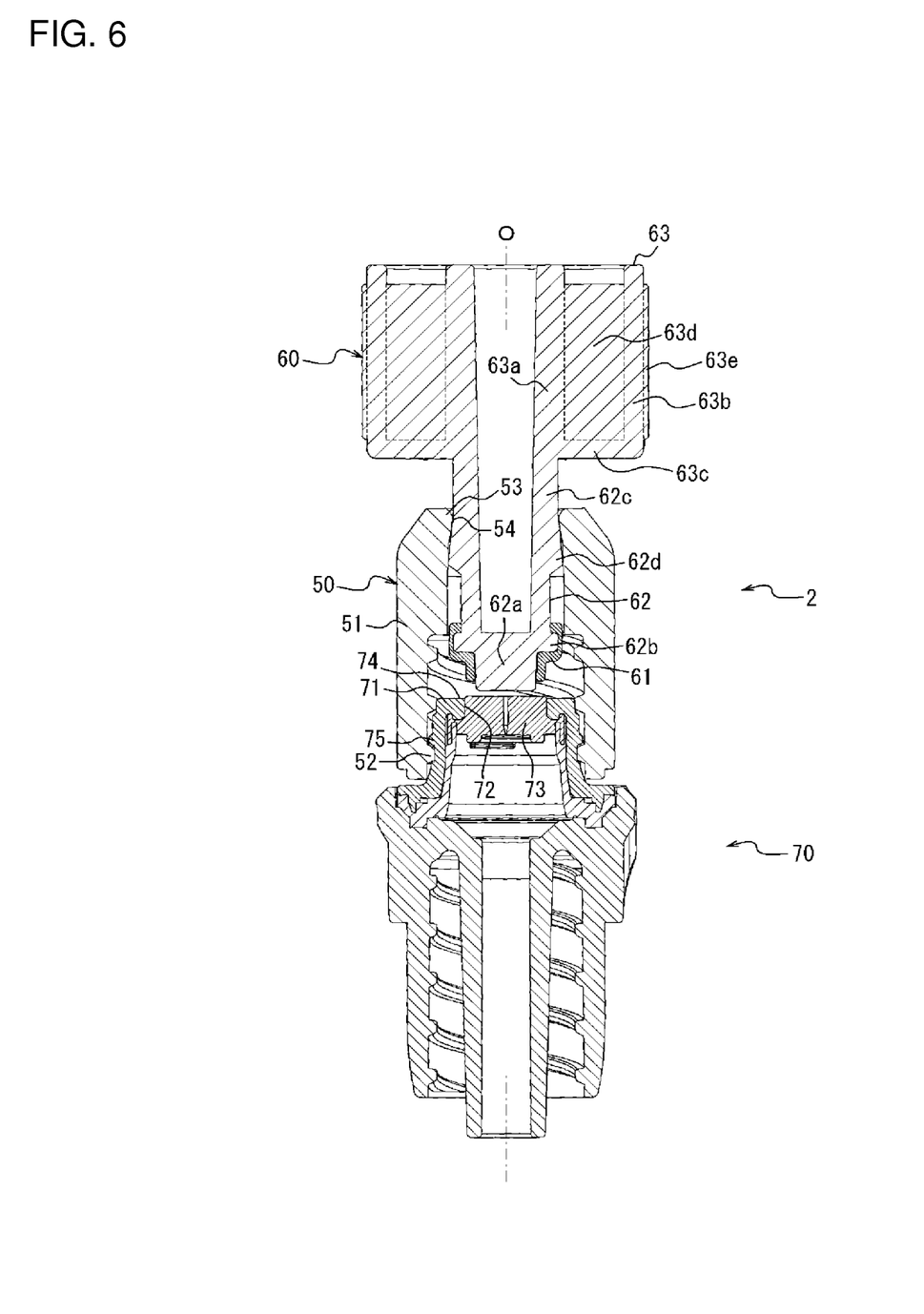
FIG. 6 is a longitudinal sectional view illustrating a state in which a disinfection cap according to another exemplary embodiment of the disclosure is attached to another example of a medical connector.

As illustrated in FIGS. 1 and 2, a disinfection cap 1 according to the exemplary embodiment of the disclosure is provided with a cap main body 20 and a wiping body 30 which is held by the cap main body 20 and used for wiping a medical connector 40 as illustrated in FIG. 3. In this example, the medical connector 40 is configured as a three-way stopcock which includes three connection sections and a flow path switching section. However, the medical connector 40 is not limited to such a configuration. For example, the medical connector 40 may be configured as a T-type port which includes three connection sections, but includes no flow path switching section or a mixed injection plug which includes two connection sections as illustrated in FIG. 6.

The medical connector 40 is provided with a male connector connection section 44 in which a valve body 43 which blocks an opening 42 of a top face wall 41 is pushed in to form a flow path when a male connector (not illustrated) is connected thereto and also provided with a medical connector side locking section which prevents pullout of the male connector by engagement with a male connector side locking section.

Figure 4:
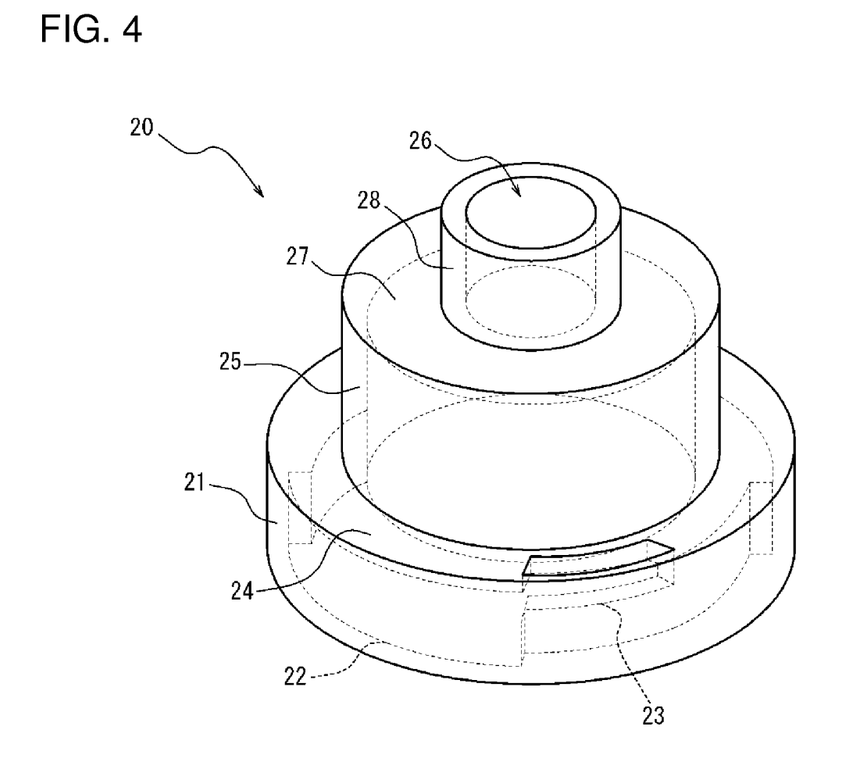
FIG. 4 is a perspective view of a cap main body in the disinfection cap of FIG. 1.

More specifically, as illustrated in FIG. 3, the medical connector 40 which is a target of the disinfection cap 1 according to the exemplary embodiment of the disclosure is provided with, as the medical connector side locking section, a set of projections 45 (two projections 45 in this example) which project from the outer peripheral face of the male connector connection section 44 toward the outer peripheral side. As illustrated in FIG. 4, the cap main body 20 includes an axial direction groove 22 and a peripheral direction groove 23 defining a cap side locking section on the inner peripheral face of a cylindrical peripheral wall 21. The axial direction groove 22 allows the set of projections 45 to pass therethrough in an axial direction. The peripheral direction groove 23 is connected to the axial direction groove 22 and allows the set of projections 45 to pass therethrough in a peripheral direction. The peripheral direction groove 23 is engaged with the set of projection 45 to prevent pullout of the cap main body 20.

The cap main body 20 includes an intermediate flange 24 which extends from the upper end of the peripheral wall 21 toward the inner peripheral side, a cylindrical annular wall 25 which rises from the inner peripheral edge of the intermediate flange 24, a top wall 27 which extends from the upper end of the annular wall 25 toward the inner peripheral side and has a circular through hole 26 on the center thereof, and a cylindrical tubular wall 28 which rises from the inner peripheral edge of the top wall 27. The cap main body 20 is made of, for example, a rigid material such as a synthetic resin.

Figure 5:
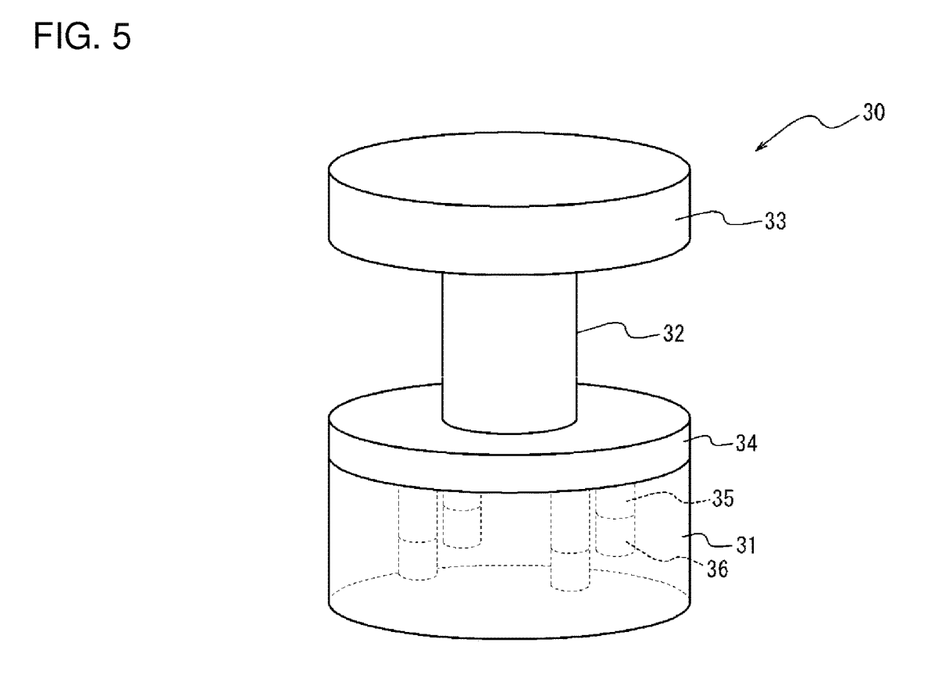
FIG. 5 is a perspective view of a wiping body in the disinfection cap of FIG. 1.

As illustrated in FIGS. 1 and 5, the wiping body 30 includes an impregnation material 31 as an impregnation section which is impregnated with an antiseptic solution, a coupling section 32 which passes through the through hole 26 formed in the cap main body 20, and an operation section 33 which is coupled to the impregnation section (the impregnation material 31 in this example) through the coupling section 32. The impregnation material 31 includes, for example, sponge and nonwoven fabric. The coupling section 32 and the operation section 33 are made of, for example, a rigid material such as a synthetic resin. The impregnation material 31 is attached to one end of the coupling section 32, the one end being configured as a disc-shaped flange 34 with, for example, an adhesive. The impregnation material 31 has a plurality of recesses 36, and a plurality of projections 35 (four projections 35 in this example) which project from the lower face of the flange 34 are inserted into the respective recesses 36 to improve followability to the rotation of the coupling section 32 to improve a wiping effect.

The operation section 33 which is coupled to the other end of the coupling section 32 has a disc-like shape having a larger diameter than the cylindrical coupling section 32. During wiping, the operation section 33 is held with fingers and operated to rotate the wiping body 30. The coupling section 32 may have a columnar shape or a polygonal columnar shape instead of the cylindrical shape. In the disinfection cap 1, the configuration of each member of the wiping body 30 and the cap main body 20 (refer to FIG. 2) may be appropriately determined in view of the productivity thereof. Specifically, for example, the cap main body 20 may include two members, each of which is a semicircular region part and the two semicircular region members may be adhered to each other or integrated by fitting after the wiping body 30 is assembled thereto. In such an instance, the wiping body 30 is held by the cap main body 20 by allowing the coupling section 32 to pass through the through hole 26. Alternatively, the coupling section 32 and the operation section 33 of the wiping body 30 may be configured as separate members and the operation section 33 may be adhered to the coupling section 32 or integrated with the coupling section 32 by fitting after the coupling section 32 is allowed to pass through the through hole 26.

In the disinfection cap 1 according to the exemplary embodiment having such a configuration, as illustrated in FIG. 1, it is possible to engage the cap side locking section (the peripheral direction groove 23 in this example) of the cap main body 20 with the medical connector side locking section (the set of projections 45 in this example) to prevent pullout of the cap main body 20 and, in this state, move the wiping body 30 with respect to the cap main body 20 to wipe the surface of the top face wall 41 and the surface of the valve body 43 in the male connector connection section 44 with the impregnation section (the impregnation material 31 in this example). Thus, the disinfection cap 1 enables stable and sufficient wiping.

In the disinfection cap 1, the wiping body 30 is rotatable around an axis O of the male connector connection section 44 with respect to the cap main body 20 with the cap side locking section (the peripheral direction groove 23 in this example) engaged with the medical connector side locking section (the set of projections 45 in this example). Thus, various germs and dirt can be efficiently wiped off by rotation of the wiping body 30.

Further, in the disinfection cap 1, the wiping body 30 is movable along the axis O of the male connector connection section 44 with respect to the cap main body 20 with the cap side locking section (the peripheral direction groove 23 in this example) engaged with the medical connector side locking section (the set of projections 45 in this example). Thus, various germs and dirt can be more reliably wiped off by pressing the wiping body 30 against the male connector connection section 44.

Further, in the disinfection cap 1, the wiping body 30 includes the operation section 33 which is coupled to the impregnation section (the impregnation material 31 in this example) through the coupling section 32 which passes through the through hole 26 formed on the cap main body 20. Thus, when the operation section 33 is operated for wiping, a movement range of the wiping body 30 can be restricted by the through hole 26. Accordingly, the wiping can be more stably performed.

Next, a disinfection cap 2 according to another exemplary embodiment of the disclosure will be described in detail as an example with reference to FIGS. 6 to 9.

As illustrated in FIG. 6, the disinfection cap 2 according to the exemplary embodiment is provided with a cap main body 50 and a wiping body 60 which is held by the cap main body 50 and used for wiping a medical connector 70 as illustrated. In this example, the medical connector 70 is configured as a mixed injection plug which includes two connection sections. However, the medical connector 70 is not limited to such a configuration. For example, the medical connector 70 may be configured as a three-way stopcock as illustrated in FIG. 1 or a T-type port.

The medical connector 70 is provided with a male connector connection section 74 in which a valve body 73 which blocks an opening 72 of a top face wall 71 is pushed in to form a flow path when a male connector (not illustrated) is connected thereto and also provided with a medical connector side locking section which prevents pullout of the male connector by engagement with a male connector side locking section.

More specifically, as illustrated in FIG. 6, the medical connector 70 which is a target of the disinfection cap 2 according to the exemplary embodiment is provided with, as the medical connector side locking section, an external thread 75 for luer lock which is formed on the outer peripheral face of the male connector connection section 74. The cap main body 50 includes an internal thread 52 for luer lock which is formed on the inner peripheral face of a cylindrical peripheral wall 51. The internal thread 52 serves as a cap side locking section which prevents pullout of the cap main body 50 by engagement with the external thread 75.

The cap main body 50 further includes an inward-facing annular projection 53 which projects toward the inner peripheral side on the upper end of the inner peripheral face of the cylindrical peripheral wall 51. The surface of the inward-facing annular projection 53 forms a circular through hole 54. The cap main body 50 is made of, for example, a rigid material such as a synthetic resin.

Figure 7:
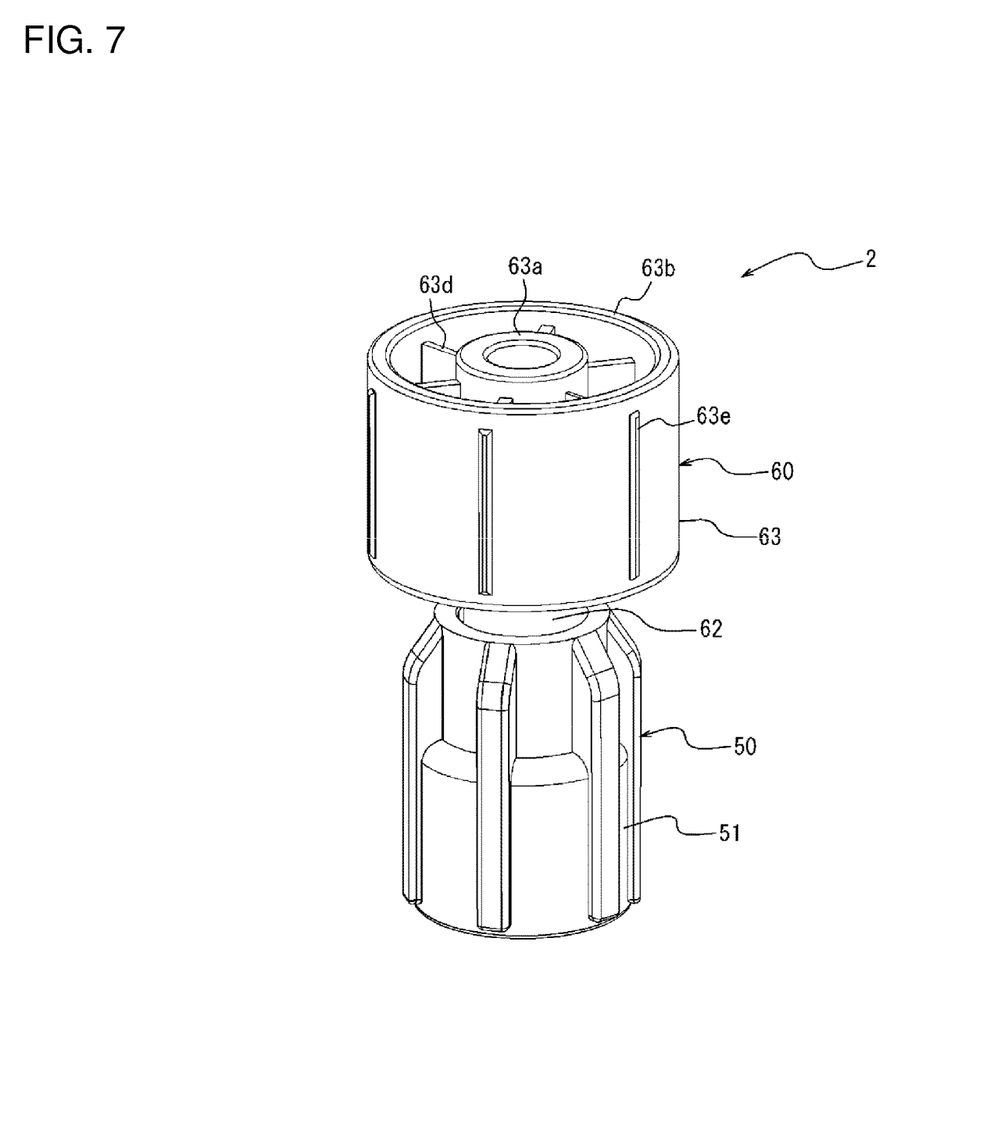
FIG. 7 is a perspective view of the disinfection cap of FIG. 6.
Figure 8:
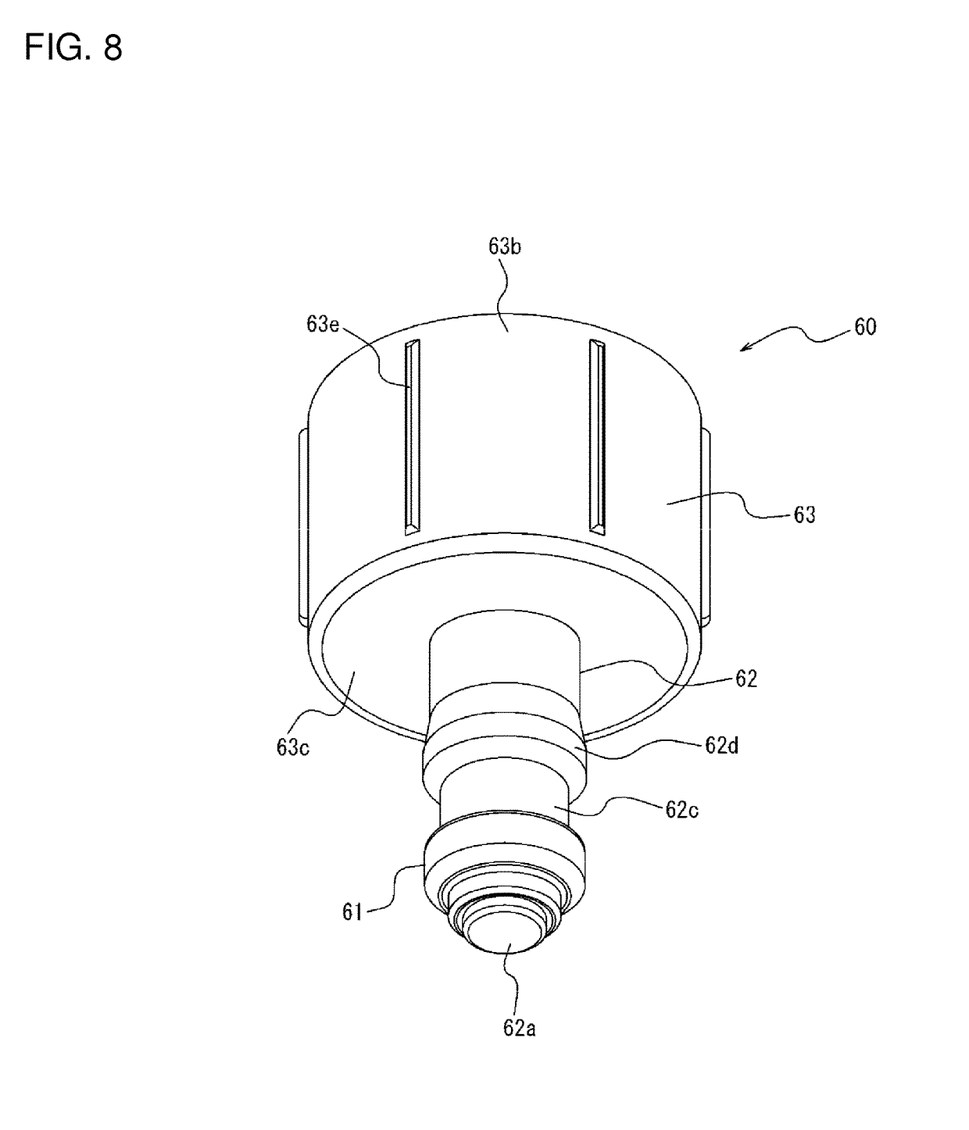
FIG. 8 is a perspective view of a wiping body in the disinfection cap of FIG. 6.

As illustrated in FIGS. 6 to 8, the wiping body 60 includes an impregnation material 61 as an impregnation section which is impregnated with an antiseptic solution, a coupling section 62 which passes through the through hole 54 formed on the cap main body 50, and an operation section 63 which is coupled to the impregnation section (the impregnation material 61 in this example) through the coupling section 62. The impregnation material 61 includes, for example, sponge and nonwoven fabric. The coupling section 62 and the operation section 63 are made of, for example, a rigid material such as a synthetic resin.

An end part (lower end part) of the coupling section 62 forms a small-diameter columnar section 62a which has a smaller diameter than the opening 72 of the top face wall 71. A large-diameter columnar section 62b which has a larger diameter than the opening 72 of the top face wall 71 is continuous with the upper end of the small-diameter columnar section 62a. A cylindrical section 62c connects the upper end of the large-diameter columnar section 62b to the operation section 63. The impregnation material 61 is attached to the outer peripheral face of the small-diameter columnar section 62a and the surface of the large-diameter columnar section 62b with, for example, an adhesive.

An outward-facing annular projection 62d, having a larger diameter than the opening diameter of the through hole 54, is formed in an intermediate part in the upper-lower direction on the outer peripheral face of the cylindrical section 62c. As illustrated in FIG. 6, a lower part of the outward-facing annular projection 62d and an upper part of the inward-facing annular projection 53 are formed in tapered shapes. Accordingly, the outward-facing annular projection 62d engages the inward-facing annular projection 53 by pressing the wiping body 60 against the cap main body 50 from the upper side so that the wiping body 60 is assembled to the cap main body 50.

As illustrated in FIGS. 6 to 8, the operation section 63 which is coupled to the base end (upper end) of the coupling section 62 includes an inner cylindrical section 63a and an outer cylindrical section 63b which are concentrically arranged, a bottom flange 63c, and a plurality of vertical ribs 63d which are arranged at intervals in the peripheral direction. The inner cylindrical section 63a and the outer cylindrical section 63b are coupled to each other by the bottom flange 63c and the vertical ribs 63d. A plurality of nonslip projections 63e are formed on the outer peripheral face of the outer cylindrical section 63b. The nonslip projections 63e serve as a slip resistance when the operation section 63 is held with fingers and operated to rotate for wiping. The nonslip projections 63e are arranged at intervals in the peripheral direction and configured as a plurality of linear projections each of which extends in the axial direction.

Figure 9:
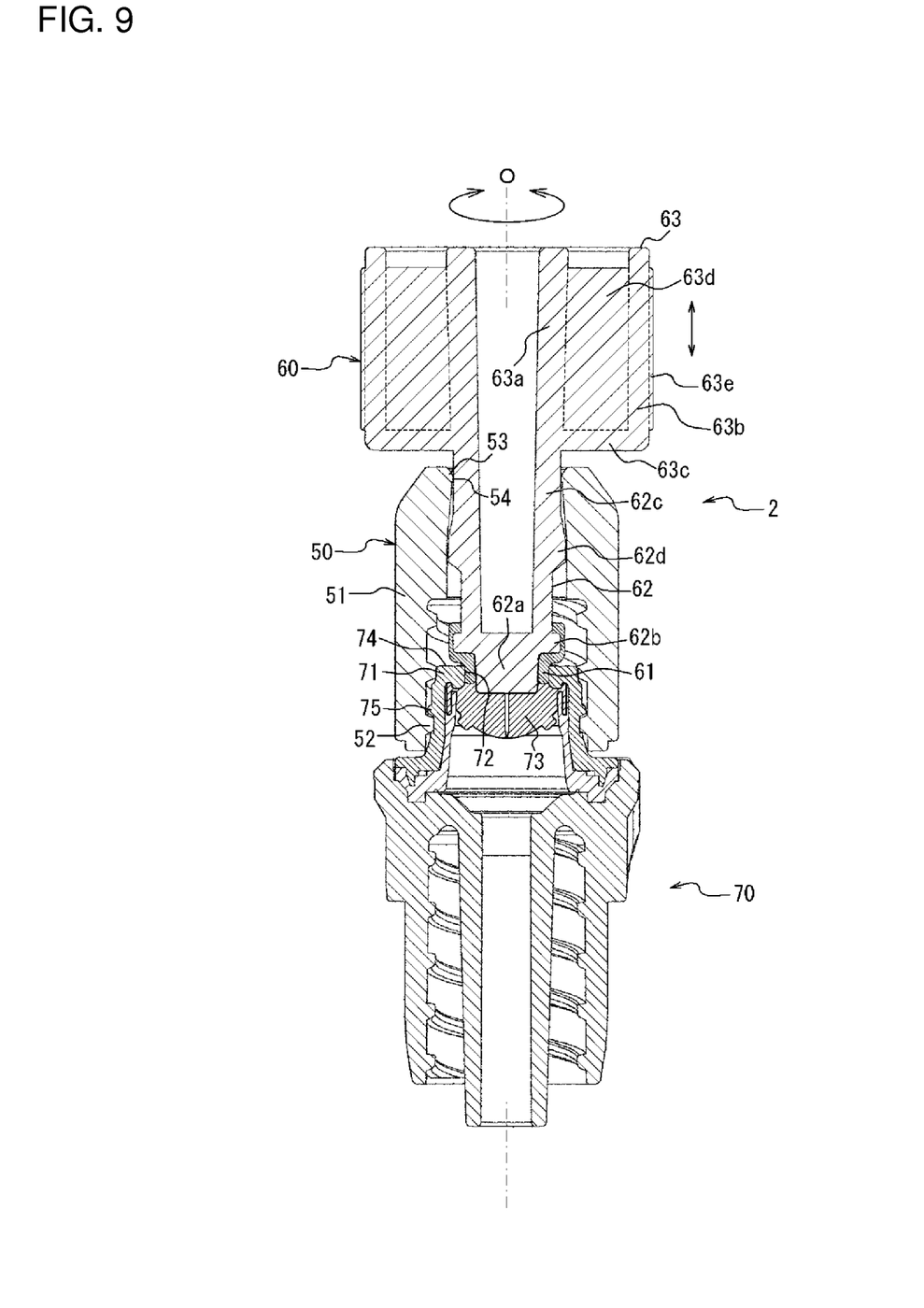
FIG. 9 is a longitudinal sectional view illustrating a state of the disinfection cap of FIG. 6 during wiping.

In the disinfection cap 2 according to the exemplary embodiment having such a configuration, as illustrated in FIG. 9, it is possible to engage the cap side locking section (the internal thread 52 in this example) of the cap main body 50 with the medical connector side locking section (the external thread 75 in this example) to prevent pullout of the cap main body 50 and, in this state, move the wiping body 60 with respect to the cap main body 50 to wipe the surface of the top face wall 71 and the inner peripheral face of the opening 72 of the top face wall 71 in the male connector connection section 74 with the impregnation section (the impregnation material 61 in this example). Thus, the disinfection cap 2 enables stable and sufficient wiping.

In the disinfection cap 2, the wiping body 60 is rotatable around an axis O of the male connector connection section 74 with respect to the cap main body 50 with the cap side locking section (the internal thread 52 in this example) engaged with the medical connector side locking section (the external thread 75 in this example). Thus, various germs and dirt can be efficiently wiped off by rotation of the wiping body 60.

Further, in the disinfection cap 2, the wiping body 60 is movable along the axis O of the male connector connection section 74 with respect to the cap main body 50 with the cap side locking section (the internal thread 52 in this example)

engaged with the medical connector side locking section (the external thread 75 in this example). Thus, various germs and dirt can be more reliably wiped off by pressing the wiping body 60 against the male connector connection section 74.

Further, in the disinfection cap 2, the wiping body 60 is movable with respect to the cap main body 50 so as to wipe at least the inner peripheral face of the opening 72 of the top face wall 71 with the impregnation section (the impregnation material 61 in this example) with the cap side locking section (the internal thread 52 in this example) engaged with the medical connector side locking section (the external thread 75 in this example). Thus, it is possible to easily wipe the inner peripheral face of the opening 72 of the top face wall 71 which is normally difficult to wipe.

Further, in the disinfection cap 2, the wiping body 60 includes the operation section 63 which is coupled to the impregnation section (the impregnation material 61 in this example) through the coupling section 62 which passes through the through hole 54 formed on the cap main body 50. Thus, when the operation section 63 is operated for wiping, a movement range of the wiping body 60 can be restricted by the through hole 54. Accordingly, the wiping can be more stably performed.

The movement range of the wiping body 60 is preferably restricted to a range that prevents an antiseptic solution impregnated in the impregnation section (the impregnation material 61 in this example) from entering the flow path of the medical connector 70. When the movement range of the wiping body 60 is restricted in such a range, movement of the wiping body 60 toward the medical connector 70 may be restricted by abutment of the large-diameter columnar section 62b against the top face wall 71 through the impregnation material 61 or abutment of the operation section 63 against the cap main body 50.

The above description shows merely exemplary embodiments of the disclosure herein, and various modifications may be made within the scope of the claims. For example, in the embodiment described with reference to FIGS. 1 to 5, the surface of the top face wall 41 and the surface of the valve body 43 are wiped with the impregnation section (impregnation material 31). Alternatively, for example, the shape of the impregnation section (impregnation material 31) may be modified to wipe only the surface of the top face wall 41 or only the surface of the valve body 43.

In the embodiment described with reference to FIGS. 6 to 9, the surface of the top face wall 71 and the inner peripheral face of the opening 72 of the top face wall 71 are wiped with the impregnation section (impregnation material 61). Alternatively, for example, an impregnation section (impregnation material 61) may be arranged also on the tip face (lower end face) of the small-diameter columnar section 62a on the tip of the coupling section 62 so as to also wipe the surface of the valve body 73, or an impregnation section (impregnation material 61) may be arranged only on the outer peripheral face of the small-diameter columnar section 62a to wipe only the inner peripheral face of the opening 72 of the top face wall 71.

In any of the embodiments described above, the medical connector 40, 70 having a structure in which the valve body 43, 73 is pushed open to form the flow path when the male connector is connected thereto is a wiping target of the disinfection cap 1, 2. However, the medical connector 40, 70 being a wiping target of the disinfection cap 1, 2 is not limited to one having such a structure and may have any structure as long as the valve body 43, 73 which blocks the opening 42, 72 of the top face wall 41, 71 is pushed in to form a flow path.

The detailed description above describes a disinfection cap. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A disinfection cap for a medical connector, the medical connector including a male connector connection section, in which a valve body blocking an opening of a top face wall is pushed in to form a flow path when a male connector is connected thereto and a medical connector side locking section configured to prevent pullout of the male connector by engagement with a male connector side locking section, the disinfection cap comprising:
    a cap main body including a cap side locking section configured to prevent pullout of the cap main body by engagement with the medical connector side locking section; and
    a wiping body held by the cap main body, the wiping body including an impregnation section impregnated with an antiseptic solution, a coupling section, and an operation section which is coupled to the impregnation section through the coupling section, the coupling section including an end part forming a small-diameter columnar section which has a smaller diameter than the opening of the top face wall, and a large-diameter columnar section which has a larger diameter than the opening of the top face wall and is continuous with an upper end of the small-diameter columnar section,
    wherein the wiping body is movable with respect to the cap main body so as to wipe at least a surface of the top face wall, an inner peripheral face of the opening, or a surface of the valve body in the male connector connection section with the impregnation section with the cap side locking section engaged with the medical connector side locking section; and
    wherein the wiping body is movable along an axis of the male connector connection section with respect to the cap main body with the cap side locking section engaged with the medical connector side locking section.

2. The disinfection cap according to claim 1, wherein the wiping body is rotatable around an axis of the male connector connection section with respect to the cap main body with the cap side locking section engaged with the medical connector side locking section.

3. The disinfection cap according to claim 1, wherein the wiping body is movable with respect to the cap main body so as to wipe at least the inner peripheral face of the opening with the impregnation section with the cap side locking section engaged with the medical connector side locking section.

4. The disinfection cap according to claim 1, wherein the operation section is coupled to the impregnation section through the coupling section that extends through a through hole formed on the cap main body.

5. The disinfection cap according to claim 1, wherein the cap main body is made of a rigid material.

6. The disinfection cap according to claim 1, wherein the impregnation section includes an impregnation material.

7. The disinfection cap according to claim 6, wherein the impregnation material is a sponge.

8. The disinfection cap according to claim 6, wherein the impregnation material is nonwoven.

9. The disinfection cap according to claim 1, wherein the impregnation section is attached to an outer peripheral face of the small-diameter columnar section and a surface of the large-diameter columnar section.

10. A disinfection system comprising:
   a disinfection cap including a cap main body including a cap side locking section configured to prevent pullout of the cap main body by engagement with a medical connector side locking section and a wiping body held by the cap main body, the wiping body including an impregnation section impregnated with an antiseptic solution; and
   a medical connector, the medical connector including a male connector connection section, in which a valve body blocking an opening of a top face wall is pushed in to form a flow path when a male connector is connected thereto, and the medical connector side locking section is configured to prevent pullout of the male connector by engagement with a male connector side locking section;
   wherein the wiping body further including a coupling section and an operation section which is coupled to the impregnation section through the coupling section, the coupling section including an end part forming a small-diameter columnar section which has a smaller diameter than the opening of the top face wall, and a large-diameter columnar section which has a larger diameter than the opening of the top face wall and is continuous with the upper end of the small-diameter columnar section;
   wherein the wiping body is movable with respect to the cap main body so as to wipe at least a surface of the top face wall, an inner peripheral face of the opening, or a surface of the valve body in the male connector connection section with the impregnation section with the cap side locking section engaged with the medical connector side locking section; and
   wherein the wiping body is movable along an axis of the male connector connection section with respect to the cap main body with the cap side locking section engaged with the medical connector side locking section.

11. The disinfection system according to claim 10, wherein the wiping body is rotatable around an axis of the male connector connection section with respect to the cap main body with the cap side locking section engaged with the medical connector side locking section.

12. The disinfection system according to claim 10, wherein the wiping body is movable with respect to the cap main body so as to wipe at least the inner peripheral face of the opening with the impregnation section with the cap side locking section engaged with the medical connector side locking section.

13. The disinfection system according to claim 10, wherein the operation section is coupled to the impregnation section through the coupling section that extends through a through hole formed on the cap main body.

14. The disinfection system according to claim 10, wherein the medical connector side locking mechanism includes an external thread and the cap side locking section includes an internal thread in the cap main body, the external thread engaging the internal thread to prevent pullout of the cap main body.

15. The disinfection system according to claim 14, wherein the medical connector comprises a mixed injection plug.

16. The disinfection cap according to claim 10, wherein the impregnation section is attached to an outer peripheral face of the small-diameter columnar section and a surface of the large-diameter columnar section.

* * * * *